United States Patent
Patil et al.

(10) Patent No.: US 11,436,205 B2
(45) Date of Patent: Sep. 6, 2022

(54) METHOD AND APPARATUS FOR PREDICTING PARAMETER VALUES OF DATA ENTRIES IN DATA SET

(71) Applicant: KONINKLIJKE PHILIPS N.V., Eindhoven (NL)

(72) Inventors: Meru Adagouda Patil, Bangalore (IN); Allmin Pradhap Singh Susaiyah, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 57 days.

(21) Appl. No.: 17/019,895

(22) Filed: Sep. 14, 2020

(65) Prior Publication Data

US 2021/0109908 A1    Apr. 15, 2021

(30) Foreign Application Priority Data

Oct. 14, 2019    (EP) .................................... 19203090

(51) Int. Cl.
*G06F 16/00*    (2019.01)
*G06F 16/215*    (2019.01)
(Continued)

(52) U.S. Cl.
CPC .......... *G06F 16/215* (2019.01); *G06F 16/217* (2019.01); *G06F 16/219* (2019.01); *G06F 17/18* (2013.01); *G16H 10/60* (2018.01)

(58) Field of Classification Search
CPC ...... G06F 17/18; G06F 16/215; G06F 16/217; G06F 16/219; G16H 10/60
See application file for complete search history.

(56) References Cited

U.S. PATENT DOCUMENTS

| | | | |
|---|---|---|---|
| 6,810,368 B1 * | 10/2004 | Pednault | G06F 17/18 |
| | | | 703/2 |
| 2008/0208621 A1 * | 8/2008 | Karkanias | G16H 10/60 |
| | | | 705/2 |

(Continued)

OTHER PUBLICATIONS

"Breiman and Cutler's Random Forests for Classification and Regression". Mar. 25, 2018. Version 4.6-14.

(Continued)

*Primary Examiner* — Shiow-Jy Fan

(57) ABSTRACT

According to an aspect, there is provided a computer-implemented method for processing a data set, the data set comprising respective data subsets for a plurality of subjects, each data subset comprising a plurality of data entries, each entry comprising respective parameter values for each of a plurality of parameters at a respective time point, wherein for a first data subset relating to a first subject in the plurality of subjects, one or more parameter values for at least a first parameter in the plurality of parameters is missing from the first data subset, the method comprising, for a first missing parameter value in a first data entry in the first data subset (a) determining completeness scores for the first parameter, wherein each completeness score indicates a level of completeness of the data entries in the first data subset for the first parameter and a respective one of the other parameters in the plurality of parameters; (b) determining correlation scores for the first parameter, wherein each correlation score indicates a level of correlation between the parameter values in the data set for the first parameter and the parameter values in the data set for a respective one of the other parameters in the plurality of parameters; (c) determining a subset of the plurality of parameters to use to form regression trees based on the determined completeness scores and the determined correlation scores; (d) forming a plurality of regression trees, (Continued)

Patient 1

| | BPSys | BPDia | Pulse | Resp | Height | Weight | Temp |
|---|---|---|---|---|---|---|---|
| 0 | 120 | 76 | 65 | 15 | 163 | 65 | 38 |
| 1 | 118 | 74 | 68 | 14 | NaN | NaN | 38 |
| 2 | 121 | 73 | 76 | 17 | 164 | 65 | 38 |
| 3 | 115 | 72 | NaN | 14 | 174 | 72 | 38 |
| 4 | NaN | NaN | 72 | 14 | 171 | 71 | 38 |
| 5 | NaN | 74 | 72 | 16 | 177 | NaN | 39 |
| 6 | NaN | 73 | NaN | 14 | 167 | 68 | 37 |
| 7 | 119 | 70 | 71 | NaN | 169 | NaN | 39 |
| 8 | 114 | 70 | 69 | 14 | 164 | 63 | 38 |
| 9 | 123 | 74 | 72 | 16 | 171 | 72 | 36 |
| 10 | 125 | 74 | NaN | NaN | 170 | 71 | 38 |

34 wherein each regression tree relates to a respective parameter combination of the first parameter and one or more of the other parameters in the determined subset, and each regression tree is trained to predict a parameter value for the first parameter based on input parameter values for the one or more other parameters in the parameter combination, wherein each regression tree is trained using training data comprising parameter values for the parameters in the respective parameter combination, wherein the training data includes the parameter values in any data entry in the first data subset for which a parameter value is present for all of the parameters in the respective parameter combination; (e) using each regression tree to predict a parameter value for the first parameter based on parameter values in the first data entry for the one or more other parameters in the parameter combination; and (f) combining the predicted parameter values to estimate the first missing parameter value. A corresponding apparatus and computer program product are also provided.

20 Claims, 13 Drawing Sheets

(51) Int. Cl.
*G16H 10/60* (2018.01)
*G06F 16/21* (2019.01)
*G06F 17/18* (2006.01)

(56) References Cited

U.S. PATENT DOCUMENTS

| | | | |
|---|---|---|---|
| 2013/0073594 A1* | 3/2013 | Jugulum | G06Q 40/00 707/802 |
| 2014/0279754 A1* | 9/2014 | Barsoum | G06N 20/00 706/12 |
| 2019/0019109 A1* | 1/2019 | Sadaghiani | G06N 5/003 |
| 2019/0179983 A1* | 6/2019 | Prochnow | E21B 41/00 |
| 2021/0087921 A1* | 3/2021 | Prochnow | E21B 43/00 |

OTHER PUBLICATIONS

Therneau, T.M. et al., "An Introduction to Recursive Partitioning Using the RPART Routines". Feb. 23, 2018.
Rahman et al., "A Decision Tree-based Missing Value Imputation Technique for Data Pre-processing". Centre for Research in Complex System, Proceedings of the 9th Australasian Data Mining Conference, Australia. (2011).
Williams, C.K. et al., "Autoencoders and Probabilistic Inference with Missing Data; An Exact Solution for the Factor Analysis Case". Alan Turing Institute, London, Sep. 5, 2018.
Patil, R.B. et al., "Predictive modeling for corrective maintenance of imaging devices from machine logs," 2017 39th Annual International Conference of the IEEE Engineering in Medicine and Biology Society (EMBC), Seogwipo, 1027, pp. 1676-1679.

* cited by examiner

| | BPSys | BPDia | Pulse | Resp | Height | Weight | Temp |
|---|---|---|---|---|---|---|---|
| 0 | 120 | 76 | 65 | 15 | 163 | 65 | 38 |
| 1 | 118 | 74 | 68 | 14 | 165 | 65 | 38 |
| 2 | 121 | 73 | 76 | 17 | 164 | 65 | 38 |
| 3 | 115 | 72 | 71 | 14 | 174 | 72 | 38 |
| 4 | 120 | 73 | 72 | 14 | 171 | 71 | 38 |
| 5 | 116 | 74 | 72 | 16 | 177 | 80 | 39 |
| 6 | 117 | 73 | 68 | 14 | 167 | 68 | 37 |
| 7 | 119 | 70 | 71 | 15 | 169 | 76 | 39 |
| 8 | 114 | 70 | 69 | 14 | 164 | 63 | 38 |
| 9 | 123 | 74 | 72 | 16 | 171 | 72 | 36 |
| 10 | 125 | 74 | 65 | 15 | 170 | 71 | 38 |

Fig. 2

| Patient 1 | | | | | | |
|---|---|---|---|---|---|---|
| | BPDia | Pulse | Resp | Height | Weight | Temp |
| 0 | 76 | 65 | 15 | 163 | 65 | 38 |
| 1 | 74 | 68 | 14 | 165 | 65 | 38 |
| 2 | 73 | 76 | 17 | 164 | 65 | 38 |
| 3 | 72 | 71 | 14 | 174 | 72 | 38 |
| 4 | 73 | 72 | 14 | 171 | 71 | 38 |
| 5 | 74 | 72 | 16 | 177 | 80 | 39 |
| 6 | 73 | 68 | 14 | 167 | 68 | 37 |
| 7 | 70 | 71 | 15 | 169 | 76 | 39 |
| 8 | 70 | 69 | 14 | 164 | 63 | 38 |
| 9 | 74 | 72 | 16 | 171 | 72 | 36 |
| 10 | 74 | 65 | 15 | 170 | 71 | 38 |

Fig. 5

| Patient 1 | | | | | | | |
|---|---|---|---|---|---|---|---|
|  | BPSys | BPDia | Pulse | Resp | Height | Weight | Temp |
| 0 | 120 | 76 | 65 | 15 | 163 | 65 | 38 |
| 1 | 118 | 74 | 68 | 14 | NaN | NaN | 38 |
| 2 | 121 | 73 | 76 | 17 | 164 | 65 | 38 |
| 3 | 115 | 72 | NaN | 14 | 174 | 72 | 38 |
| 4 | NaN | NaN | 72 | 14 | 171 | 71 | 38 |
| 5 | NaN | 74 | 72 | 16 | NaN | NaN | 39 |
| 6 | NaN | 73 | NaN | 14 | 177 | 68 | 37 |
| 7 | 119 | 70 | 71 | NaN | 167 | NaN | 39 |
| 8 | 114 | 70 | 69 | 14 | 169 | 63 | 38 |
| 9 | 123 | 74 | 72 | 16 | 164 | 72 | 36 |
| 10 | 125 | 74 | NaN | NaN | 171 | 71 | 38 |

Fig. 7

| Patient 1 | | | | | | |
|---|---|---|---|---|---|---|
| | BPDia | Pulse | Resp | Height | Weight | Temp |
| 0 | 76 | 65 | 15 | 163 | 65 | 38 |
| 2 | 73 | 76 | 17 | 164 | 65 | 38 |
| 8 | 70 | 69 | 14 | 164 | 63 | 38 |
| 9 | 74 | 72 | 16 | 171 | 72 | 36 |

| Patient 1 | |
|---|---|
| | BPSys |
| 0 | 120 |
| 2 | 121 |
| 8 | 114 |
| 9 | 123 |

| BPSys | BPDia | Pulse | Resp | Height | Weight | Temp |
|---|---|---|---|---|---|---|
| NaN | 73 | NaN | 14 | 167 | 68 | 37 |

(a)

| BPSys | BPDia | Resp | Pulse |
|---|---|---|---|
| 120 | 76 | 15 | 65 |
| 118 | 74 | 14 | 68 |
| 121 | 73 | 17 | 76 |
| 114 | 70 | 14 | 69 |
| 123 | 74 | 16 | 72 |

(b)

| BPSys | BPDia | Pulse |
|---|---|---|
| 120 | 76 | 65 |
| 118 | 74 | 68 |
| 121 | 73 | 76 |
| 119 | 70 | 71 |
| 114 | 70 | 69 |
| 123 | 74 | 72 |

(c)

| BPSys | Pulse |
|---|---|
| 120 | 65 |
| 118 | 68 |
| 121 | 76 |
| 119 | 71 |
| 114 | 69 |
| 123 | 72 |

(d)

| BPDia | Pulse |
|---|---|
| 76 | 65 |
| 74 | 68 |
| 73 | 76 |
| 74 | 72 |
| 70 | 71 |
| 70 | 69 |
| 74 | 72 |

Fig. 13

| Patient 1 | BPSys | BPDia | Pulse | Resp | Height | Weight | Temp |
|---|---|---|---|---|---|---|---|
| 0 | 120 | 76 | 65 | 15 | 163 | 65 | 38 |
| 1 | 118 | 74 | 68 | 14 | 163 | 61 | 38 |
| 2 | 121 | 73 | 76 | 17 | 164 | 65 | 38 |
| 3 | 115 | 72 | 69 | 14 | 174 | 72 | 38 |
| 4 | 122 | 69 | 72 | 14 | 171 | 71 | 38 |
| 5 | 121 | 74 | 72 | 16 | 177 | 79 | 39 |
| 6 | 120 | 73 | 66 | 14 | 167 | 68 | 37 |
| 7 | 119 | 70 | 71 | 15 | 169 | 70 | 39 |
| 8 | 114 | 70 | 69 | 14 | 164 | 63 | 38 |
| 9 | 123 | 74 | 72 | 16 | 171 | 72 | 36 |
| 10 | 125 | 74 | 75 | 15 | 170 | 71 | 38 |

Patient 1

| | BPSys | BPDia | Pulse | Resp | Height | Weight | Temp |
|---|---|---|---|---|---|---|---|
| 0 | 120 | 76 | 65 | 15 | 163 | 65 | 38 |
| 1 | 118 | 74 | 68 | 14 | 170 | 61 | 38 |
| 2 | 121 | 73 | 76 | 17 | 164 | 65 | 38 |
| 3 | 115 | 72 | 72 | 14 | 174 | 72 | 38 |
| 4 | 120 | 70 | 72 | 14 | 171 | 71 | 38 |
| 5 | 121 | 74 | 72 | 16 | 177 | 80 | 39 |
| 6 | 119 | 73 | 70 | 14 | 167 | 68 | 37 |
| 7 | 119 | 70 | 71 | 16 | 169 | 72 | 39 |
| 8 | 114 | 70 | 69 | 14 | 164 | 63 | 38 |
| 9 | 123 | 74 | 72 | 16 | 171 | 72 | 36 |
| 10 | 125 | 74 | 75 | 18 | 170 | 71 | 38 |

METHOD AND APPARATUS FOR PREDICTING PARAMETER VALUES OF DATA ENTRIES IN DATA SET

FIELD OF THE INVENTION

The disclosure relates to the processing of a data set that has one or more parameter values that are missing, and in particular to a computer-implemented method, apparatus and computer program product for processing the data set to estimate one or more of the missing parameter value(s).

BACKGROUND OF THE INVENTION

Missing value imputation is a technique for replacing data (parameter values) that are missing from a data set with substituted values. This is one of the techniques often used as part of data pre-processing. As data sets acquired in real-life scenarios are rarely complete and 'ready to use', data pre-processing needs to be carried out before activities like building machine/deep learning models using the data set or conducting statistical data analysis.

Some examples of data sets where parameter values may be missing include (but are not limited to): log or sensor data collected from machines or devices, such as medical devices, that can be used for predictive analysis of the failure of components in the machine or device; sensor data collected from different locations for use in weather prediction; measurements of vital parameters or physiological characteristics of a patient in a healthcare setting (e.g. an intensive care unit, ICU). In these examples parameter values may be continuously or periodically collected from the machines, devices and/or sensors.

Large medical device original equipment manufacturers (OEMs) collect log or sensor data for machines or devices to predict failure of critical components well before they actually fail at a customer's site. This task can be accomplished by data analytics of error patterns and building machine learning based models. Typically, in these scenarios the data analysis can be done in the temporal domain, as degradation of device performance happens over time. As data is typically needed across multiple days, there can be a practical issue in obtaining all of the required measurements for all of the machines or devices. For example a machine or device could be temporarily disconnected from a network, e.g. due to network connection issues or a power outage, some of the data may be corrupted during transfer across the network, or one or more sensors may become faulty. In some examples some of the measurements may be entered manually by a user (e.g. a care provider in a healthcare setting), and it is possible that the user may forget to record or input one or more measurements from time to time (e.g. typically a care provider takes a blood pressure measurement of the patient, however due to workload certain measurements can be missed by the care provider).

The above examples and problems can result in a data set that has one or more missing parameter values. The data set may relate to one or more subjects, where a subject can be a person (e.g. a patient), or an object, such as a device or machine, and includes values of parameters of the subject that are measured or observed over time.

There are several ways to handle data sets that have one or more missing parameter values. One methodology is to ignore any values for the parameter in some parts of the data analysis. However this approach does not always work well, as if the number of missing parameter values is low, then potentially a lot of useful data may be discarded or ignored.

A second issue is that the parameter may be important, and/or only have a small sample size (e.g. measurements of device failure, or measurements of rare diseases), and so any reduction in the amount of data relating to these parameter(s) in the analysis will potentially negate the purpose of measuring these parameter values in the first place.

Therefore there is need for imputing or estimating missing parameter values. One of the simplest techniques for imputing parameter values is to fill in a missing parameter value according to the average parameter value of the parameter under consideration (e.g. a missing heart rate value can be estimated as the average of all of the other measured heart rate values of the subject, or estimated as the average of all measured heart rate values for all subjects). However this has the issue that the average value will only capture the global trend of the parameter, and miss variations that may have actually occurred at a given time.

To solve this issue, weighted mean based imputation techniques or windows based average imputation techniques have been developed where a missing parameter value is estimated based on a weighted average of the parameter values of the parameter under consideration, or an average of values of the parameter within a window (i.e. a short time period). However these techniques also fail in cases where there is a sudden increase or decrease in the parameter values.

Improvements in the estimation of missing values in a data set are therefore desired.

SUMMARY OF THE INVENTION

The techniques described herein make use of completeness information and correlation information across dependent parameters (i.e. parameters whose values have some dependency on the values of other parameters) and builds dynamic decision trees to estimate the missing value. In some embodiments auto encoder techniques are used to refine the estimate of a missing parameter value.

According to a first aspect, there is provided a computer-implemented method for processing a data set. The data set comprises respective data subsets for a plurality of subjects, each data subset comprising a plurality of data entries, each entry comprising respective parameter values for each of a plurality of parameters at a respective time point. For a first data subset relating to a first subject in the plurality of subjects, one or more parameter values for at least a first parameter in the plurality of parameters is missing from the first data subset. The method comprises, for a first missing parameter value in a first data entry in the first data subset: (a) determining completeness scores for the first parameter, wherein each completeness score indicates a level of completeness of the data entries in the first data subset for the first parameter and a respective one of the other parameters in the plurality of parameters; (b) determining correlation scores for the first parameter, wherein each correlation score indicates a level of correlation between the parameter values in the data set for the first parameter and the parameter values in the data set for a respective one of the other parameters in the plurality of parameters; (c) determining a subset of the plurality of parameters to use to form regression trees based on the determined completeness scores and the determined correlation scores; (d) forming a plurality of regression trees, wherein each regression tree relates to a respective parameter combination of the first parameter and one or more of the other parameters in the determined subset, and each regression tree is trained to predict a parameter value for the first parameter based on input parameter values for the one or more other parameters in the parameter combination, wherein each regression tree is trained using training data comprising parameter values for the parameters in the respective parameter combination, wherein the training data includes the parameter values in any data entry in the first data subset for which a parameter value is present for all of the parameters in the respective parameter combination; (e) using each regression tree to predict a parameter value for the first parameter based on parameter values in the first data entry for the one or more other parameters in the parameter combination; and (f) combining the predicted parameter values to estimate the first missing parameter value. Thus the method provides improvements in the estimation of missing values in a data set that make use of completeness information and correlation information across dependent parameters and builds multiple regression trees to estimate the missing parameter value using as many data entries in the data set as possible.

In some embodiments, the method further comprises determining one or both of: a global average parameter value for the first parameter from all of the parameter values for the first parameter in the data set; and a local average parameter value for the first parameter from all of the parameter values for the first parameter in the first data subset; and the step of combining comprises: combining the predicted parameter values and the determined one or both of the global average parameter value and the local average parameter value to estimate the first missing parameter value.

In these embodiments, the step of combining can comprise combining the predicted parameter values and the determined one or both of the global average parameter value and the local average parameter value using a complementary filter.

In some embodiments, the step of determining completeness scores for the first parameter comprises, for each of the other parameters, determining a number of data entries in the first data subset in which a parameter value for the first parameter and a parameter value for the other parameter are both present.

In these embodiments, the step of determining completeness scores for the first parameter can further comprises, for each of the other parameters, determining the completeness score based on the determined number of data entries relative to a total number of data entries in the first data subset.

In some embodiments, the step of determining correlation scores for the first parameter comprises, for each of the other parameters, determining a covariance between the first parameter and the other parameter based on the parameter values for the first parameter and the other parameter in the data set; determining a standard deviation of the parameter values of the first parameter in the data set and a standard deviation of the parameter values of the other parameter in the data set; and determining the correlation score for the first parameter and the other parameter from the determined covariance and determined standard deviations.

In some embodiments, the step of determining a subset of the plurality of parameters to use to form regression trees comprises determining a fitness score for each of the other parameters based on the completeness score for the other parameter and the correlation score for the other parameter; and selecting other parameters for the subset based on determined fitness score for the other parameters. In this way the parameters selected for the subset are those parameters that have the best completeness scores and correlation scores.

In some embodiments, the method further comprises, prior to step (a), the step of selecting the first parameter as the parameter in the plurality of parameters that has a highest number of missing parameter values in the first data subset.

In some embodiments, the method further comprises updating the data set to include the estimated first missing parameter value. In these embodiments, the method can further comprise repeating steps (a)-(f) for at least a second missing parameter value in a second data entry in the first data subset, wherein the second missing parameter value is a parameter value of the first parameter, and wherein steps (a)-(f) are repeated using the data set updated with the estimated first missing parameter value; and updating the data set to include the estimated second missing parameter value. In this way, a previously estimated missing parameter value is included in the data set and taken into account when estimating other missing values of that parameter. In some embodiments, the method may further comprise repeating steps (a)-(f) for at least a third missing parameter value in a third data entry in the first data subset, wherein the third missing parameter value is a parameter value for another one of the plurality of parameters the first data subset for which a parameter value is missing, and steps (a)-(f) are repeated using the data set with previously estimated missing parameter values; updating the data set to include the estimated third missing parameter value. In this way, a previously estimated missing parameter value is included in the data set and taken into account when estimating other missing parameter values for other parameters.

In some embodiments, the method further comprises: repeating steps (a)-(f) for each missing parameter value in the data set, wherein steps (a)-(f) are repeated using the data set updated with previously estimated missing parameter values; and updating the data set to include each estimated missing parameter value. Thus, the method provides that all of the missing parameter values are estimated.

In these embodiments, the method can further comprise: using a trained auto encoder to determine a refined first missing parameter value, wherein the auto encoder receives as input the data set updated with each of the estimated missing parameter values. The use of the trained auto encoder enables noise that has accumulated in the estimated parameter values to be removed or reduced.

In these embodiments, the method can further comprise: training an auto encoder using an auto encoder training data set to form the trained auto encoder, wherein the auto encoder is trained such that the trained auto encoder operates to compress and then decompress the data set updated with each of the estimated missing parameter values; wherein the auto encoder training data set comprises data entries in the data set for which parameter values are present for all of the parameters. Thus the auto encoder is only trained using data entries in the data set that are complete, which improves the performance of the auto encoding process.

In these embodiments, the step of using the auto encoder can comprise the auto encoder compressing and decompressing the data set updated with each of the estimated missing parameter values to determine a refined data set; and the method can further comprise determining a corrected data set from the data set and the determined refined data set, wherein the corrected data set comprises the parameter values in the data set and the parameter values in the refined data set for the missing parameter values in the data set. In this way all of the non-missing parameter values in the data set are retained for the corrected data set, and only the outputs of the auto encoder corresponding to the missing parameter values are used.

In some embodiments, the method prior to step (a) further comprises evaluating each of the parameter values in the data set against a criteria for the respective parameter that determines whether the parameter value is corrupt; and discarding any parameter value from the data set that is determined to be corrupt and treating the discarded parameter value as a missing parameter value. In this way the method is able to deal with parameter values in the data set that are corrupted using the same method presented above for missing parameter values.

In some embodiments, each subject is a patient of a healthcare system, and the plurality of parameters relate to demographic and/or physiological information about the patient. In alternative embodiments, each subject is an electronic and/or mechanical device, and the plurality of parameters relate to operational information for the electronic and/or mechanical device.

According to a second aspect, there is provided a computer program product comprising a computer readable medium having computer readable code embodied therein, the computer readable code being configured such that, on execution by a suitable computer or processor, the computer or processor is caused to perform the method according to the first aspect or any embodiment thereof.

According to a third aspect, there is provided an apparatus for processing a data set. The data set comprises respective data subsets for a plurality of subjects, each data subset comprising a plurality of data entries, each entry comprising respective parameter values for each of a plurality of parameters at a respective time point. For a first data subset relating to a first subject in the plurality of subjects, one or more parameter values for at least a first parameter in the plurality of parameters is missing from the first data subset. The apparatus comprises a processing unit is configured to, for a first missing parameter value in a first data entry in the first data subset: (a) determine completeness scores for the first parameter, wherein each completeness score indicates a level of completeness of the data entries in the first data subset for the first parameter and a respective one of the other parameters in the plurality of parameters; (b) determine correlation scores for the first parameter, wherein each correlation score indicates a level of correlation between the parameter values in the data set for the first parameter and the parameter values in the data set for a respective one of the other parameters in the plurality of parameters; (c) determine a subset of the plurality of parameters to use to form regression trees based on the determined completeness scores and the determined correlation scores; (d) form a plurality of regression trees, wherein each regression tree relates to a respective parameter combination of the first parameter and one or more of the other parameters in the determined subset, and each regression tree is trained to predict a parameter value for the first parameter based on input parameter values for the one or more other parameters in the parameter combination, wherein each regression tree is trained using training data comprising parameter values for the parameters in the respective parameter combination, wherein the training data includes the parameter values in any data entry in the first data subset for which a parameter value is present for all of the parameters in the respective parameter combination; (e) use each regression tree to predict a parameter value for the first parameter based on parameter values in the first data entry for the one or more other parameters in the parameter combination; and (f) combine the predicted parameter values to estimate the first missing parameter value. Thus the apparatus provides improvements in the estimation of missing values in a data set that make use of completeness information and correlation information across dependent parameters and builds multiple regression trees to estimate the missing parameter value using as many data entries in the data set as possible.

In some embodiments, the processing unit is further configured to determine one or both of: a global average parameter value for the first parameter from all of the parameter values for the first parameter in the data set; and a local average parameter value for the first parameter from all of the parameter values for the first parameter in the first data subset; and the processing unit is configured to combine the predicted parameter values by combining the predicted parameter values and the determined one or both of the global average parameter value and the local average parameter value to estimate the first missing parameter value.

In these embodiments, the processing unit can be configured to combine the predicted parameter values by combining the predicted parameter values and the determined one or both of the global average parameter value and the local average parameter value using a complementary filter.

In some embodiments, the processing unit is configured to determine completeness scores for the first parameter by, for each of the other parameters, determining a number of data entries in the first data subset in which a parameter value for the first parameter and a parameter value for the other parameter are both present.

In these embodiments, the processing unit can be further configured to determine completeness scores for the first parameter by, for each of the other parameters, determining the completeness score based on the determined number of data entries relative to a total number of data entries in the first data subset.

In some embodiments, the processing unit is configured to determine correlation scores for the first parameter by, for each of the other parameters, determining a covariance between the first parameter and the other parameter based on the parameter values for the first parameter and the other parameter in the data set; determining a standard deviation of the parameter values of the first parameter in the data set and a standard deviation of the parameter values of the other parameter in the data set; and determining the correlation score for the first parameter and the other parameter from the determined covariance and determined standard deviations.

In some embodiments, the processing unit is configured to determine a subset of the plurality of parameters to use to form regression trees by determining a fitness score for each of the other parameters based on the completeness score for the other parameter and the correlation score for the other parameter; and selecting other parameters for the subset based on determined fitness score for the other parameters. In this way the parameters selected for the subset are those parameters that have the best completeness scores and correlation scores.

In some embodiments, the processing unit is further configured to, prior to operation (a), select the first parameter as the parameter in the plurality of parameters that has a highest number of missing parameter values in the first data subset.

In some embodiments, the processing unit is further configured to update the data set to include the estimated first missing parameter value. In these embodiments, the processing unit can be further configured to repeating operations (a)-(f) for at least a second missing parameter value in a second data entry in the first data subset, wherein the second missing parameter value is a parameter value of the first parameter, and wherein the processing unit is configured to repeat operations (a)-(f) using the data set updated with the estimated first missing parameter value; and updating the data set to include the estimated second missing parameter value. In this way, a previously estimated missing parameter value is included in the data set and taken into account when estimating other missing values of that parameter. In some embodiments, the processing unit can be further configured to repeat operations (a)-(f) for at least a third missing parameter value in a third data entry in the first data subset, wherein the third missing parameter value is a parameter value for another one of the plurality of parameters the first data subset for which a parameter value is missing, and operations (a)-(f) are repeated using the data set with previously estimated missing parameter values; updating the data set to include the estimated third missing parameter value. In this way, a previously estimated missing parameter value is included in the data set and taken into account when estimating other missing parameter values for other parameters.

In some embodiments, the processing unit is further configured to repeat operations (a)-(f) for each missing parameter value in the data set, wherein operations (a)-(f) are repeated using the data set updated with previously estimated missing parameter values; and updating the data set to include each estimated missing parameter value. Thus, the apparatus provides that all of the missing parameter values are estimated.

In these embodiments, the processing unit can be further configured to use a trained auto encoder to determine a refined first missing parameter value, wherein the auto encoder receives as input the data set updated with each of the estimated missing parameter values. The use of the trained auto encoder enables noise that has accumulated in the estimated parameter values to be removed or reduced.

In these embodiments, the processing unit can be further configured to: train an auto encoder using an auto encoder training data set to form the trained auto encoder, wherein the auto encoder is trained such that the trained auto encoder operates to compress and then decompress the data set updated with each of the estimated missing parameter values; wherein the auto encoder training data set comprises data entries in the data set for which parameter values are present for all of the parameters. Thus the auto encoder is only trained using data entries in the data set that are complete, which improves the performance of the auto encoding process.

In these embodiments, the processing unit is configured to use the auto encoder to compress and decompress the data set updated with each of the estimated missing parameter values to determine a refined data set; and the processing unit can be further configured to determine a corrected data set from the data set and the determined refined data set, wherein the corrected data set comprises the parameter values in the data set and the parameter values in the refined data set for the missing parameter values in the data set. In this way all of the non-missing parameter values in the data set are retained for the corrected data set, and only the outputs of the auto encoder corresponding to the missing parameter values are used.

In some embodiments, the processing unit can be further configured to, prior to operation (a), evaluate each of the parameter values in the data set against a criteria for the respective parameter that determines whether the parameter value is corrupt; and discard any parameter value from the data set that is determined to be corrupt and treating the discarded parameter value as a missing parameter value. In this way the apparatus is able to deal with parameter values in the data set that are corrupted using the same processing operations presented above for missing parameter values.

In some embodiments, each subject is a patient of a healthcare system, and the plurality of parameters relate to demographic and/or physiological information about the patient. In alternative embodiments, each subject is an electronic and/or mechanical device, and the plurality of parameters relate to operational information for the electronic and/or mechanical device.

BRIEF DESCRIPTION OF THE DRAWINGS

Exemplary embodiments will now be described, by way of example only, with reference to the following drawings, in which:

FIG. 2 illustrates an exemplary data set;

FIG. 5 illustrates exemplary training data that can be used for forming regression trees;

FIG. 7 illustrates an exemplary data set having a plurality of missing parameter values;

FIG. 8 illustrates training data in the data set of FIG. 7 that can be used for forming a regression tree for estimating BPSys;

FIG. 9 illustrates exemplary BPSys values associated with the training data in FIG. 8;

FIG. 13 illustrates exemplary training data and parameters for four regression trees;

FIG. 14 illustrates an updated data set; and

FIG. 15 illustrates a corrected data set.

DETAILED DESCRIPTION OF EMBODIMENTS

As noted above the techniques presented herein provide improvements in the estimation of missing values in a data set. In particular completeness information and correlation information across dependent parameters (i.e. parameters whose values have some dependency on the values of other parameters) are used, and dynamic regression trees are built to estimate the missing value(s).

Figure 1:
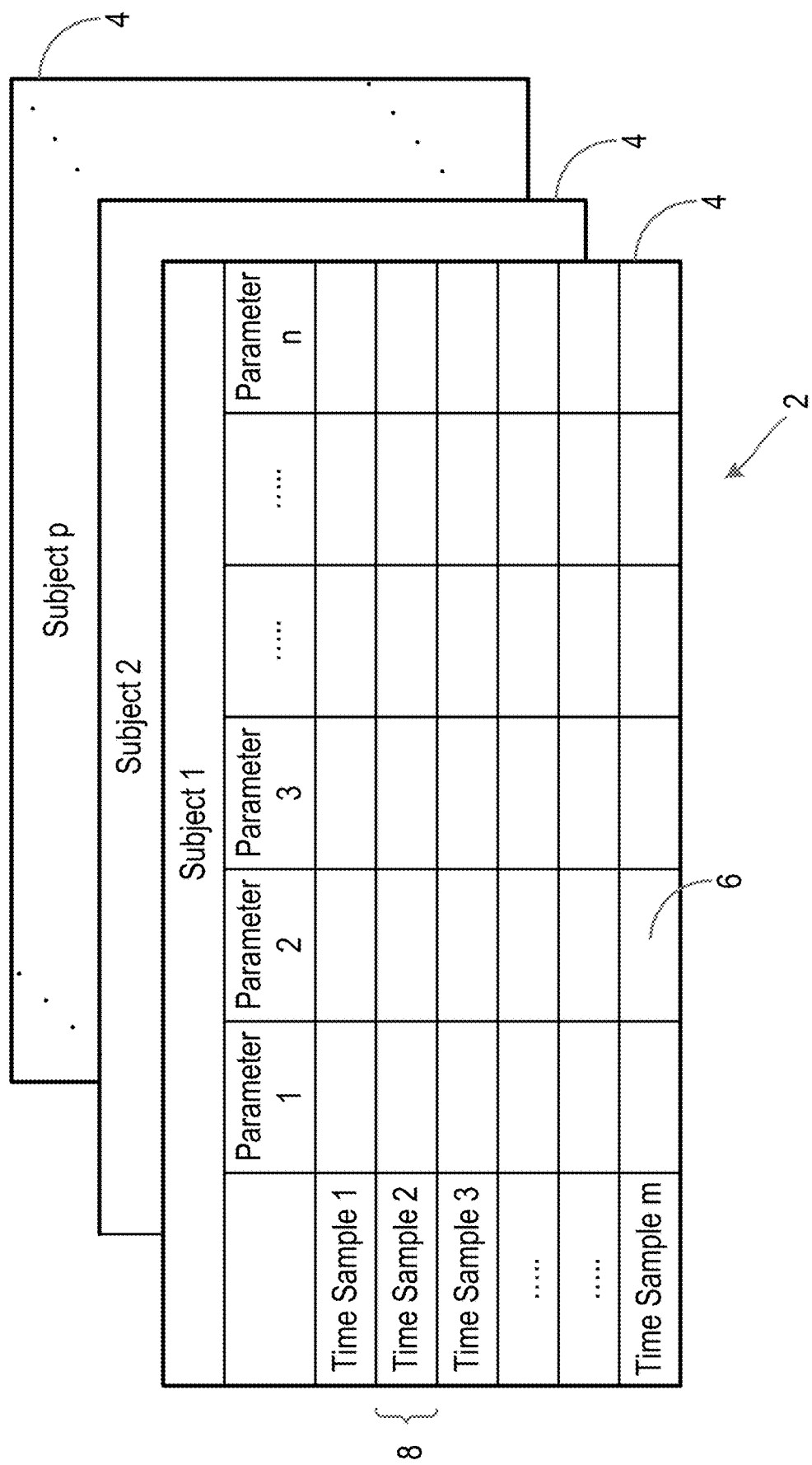
FIG. 1 illustrates a database structure for a data set to which the techniques described herein can be applied.

FIG. 1 illustrates a database structure for a data set to which the techniques described herein can be applied. The data set 2 may relate to one or more subjects, where a subject can be a person (e.g. a patient), or an object, such as a device or machine, or part of a device or a part of a machine. The number of subjects for which data is contained in the data set 2 is denoted p. The data for a particular subject p is referred to as a data subset 4, and includes values 6 ('parameter values 6') for a plurality of parameters that are measured or observed over time at a number of time points (also referred to as 'time samples'). The parameter values can be derived from multiple different sources and/or multiple different types of sources. For example, a parameter value can be an output of a sensor, a log file output from a processing unit associated with the subject, a manual input into the data set 2 by a user (e.g. healthcare provider or machine operator). The number of parameters that are observed or measured for each subject is denoted n. The parameter values 6 across the n parameters observed or measured at a particular time point is referred to as a 'data entry' 8. The number of time points at which the values of the parameters are observed or measured is denoted m, and thus there are m data entries 8 in each data subset 4. Thus, a data set 2 that is complete will comprise m×n×p parameter values 6.

In particular embodiments, each subject is a patient of a healthcare system, and the plurality of parameters relate to demographic and/or physiological information about the patient. In other particular embodiments, each subject is an electronic and/or mechanical device, and the plurality of parameters relate to operational information for the electronic and/or mechanical device. In some embodiments the electronic and/or mechanical device is a device used in the healthcare field, such as a magnetic resonance imaging (MRI) scanner, a computerised tomography (CT) scanner, or an Interventional X-ray (iXR) system.

More generally, the data set 2 shown in FIG. 1 is known as a two dimensional (2D) represented time series (2DRTS) data set, and it is a collection of data $X = \mathbb{R}^{m,n,p}$ with elements (parameter values) $x_{ijk}$, where (as noted above) n is the number of parameters, m is the number of time samples, and p is the number of subjects.

FIG. 2 illustrates an exemplary data set 10 that can originate in the healthcare field. Each subject is a patient, and the exemplary data set 10 includes a data subset 4 for each patient p. There are 7 parameters (so n=7), systolic blood pressure ('BPSys', measured in millimetres (mm) of mercury, mmHg), diastolic blood pressure ('BPDia', measured in mmHg), pulse rate ('Pulse', measured in pulses per minute, ppm), respiration rate ('resp', measured in breaths per minute, bpm), height (measured in centimetres, cm), weight (measured in kilograms, kg) and body temperature ('Temp', measured in degrees Celsius, ° C.). There are 11 data entries 8 (so m=11), so the data subset 4 includes parameter values of each parameter at 11 different time points.

The exemplary data set 10 shown in FIG. 2 is complete, i.e. it includes a parameter value for each parameter, at each time point, for each subject. However, in practice one or more parameter values may be missing from a data set 2. For example, a machine or device could be temporarily disconnected from a network, e.g. due to network connection issues or a power outage, preventing sensor measurements or log file outputs being provided to the data set 2. As another example, some of the data may be lost during transfer across the network. As another example, or one or more sensors that measure the parameter values may become faulty. As yet another example, one or more parameters may be observed and recorded manually by a user (e.g. a care provider in a healthcare setting), and it is possible that the user may forget to record or input one or more measurements from time to time.

Generally, a data set 2 has one or more missing values if, for any given k, there does not exist an $x_{ij}$ that is complete for all i, j.

Figure 3:
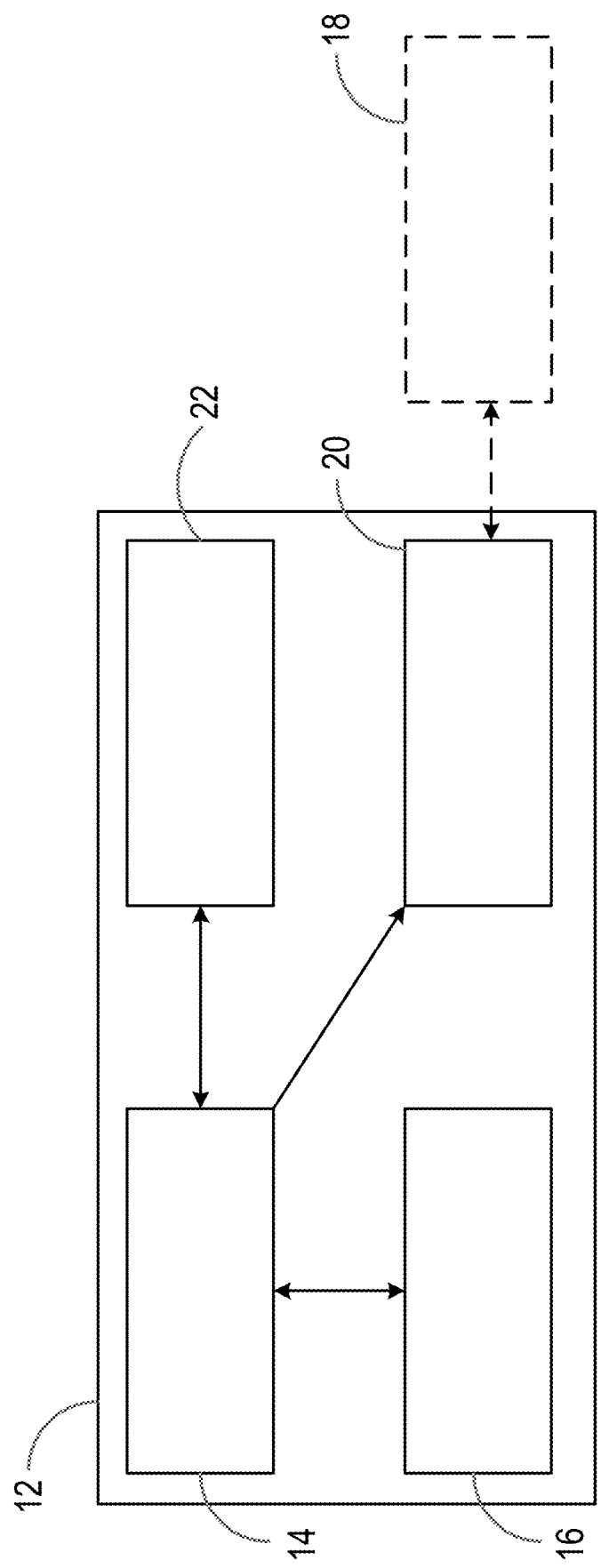
FIG. 3 is a block diagram illustrating an apparatus according to an exemplary embodiment.

Before describing the techniques for estimating missing parameter values, an apparatus is presented in FIG. 3 that can be used to implement various embodiments of the techniques.

The apparatus 12 is an electronic (e.g. computing) device that comprises a processing unit 14 and a memory unit 16. The processing unit 14 is configured or adapted to control the operation of the apparatus 12 and to implement the techniques described herein for estimating missing parameter values.

The processing unit 14 can be configured to execute or perform the methods described herein. The processing unit 14 can be implemented in numerous ways, with software and/or hardware, to perform the various functions described herein. The processing unit 14 may comprise one or more microprocessors or digital signal processor (DSPs) that may be programmed using software or computer program code to perform the required functions and/or to control components of the processing unit 14 to effect the required functions. The processing unit 14 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

The processing unit 14 is connected to a memory unit 16 that can store data, information and/or signals for use by the processing unit 14 in controlling the operation of the apparatus 12 and/or in executing or performing the methods described herein. In some implementations the memory unit 16 stores computer-readable code that can be executed by the processing unit 14 so that the processing unit 14, in conjunction with the memory unit 16, performs one or more functions, including the methods described herein. The memory unit 16 can comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM), and electrically erasable PROM (EEPROM), and the memory unit 16 can be implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

In some embodiments or implementations, the memory unit 16 stores the data set 2. In some of these embodiments or implementations, the apparatus 12 can receive the parameter values for the subject(s) from the sensor(s), device(s) and user(s) as appropriate, and store them in the data set 2 in the memory unit 16. In alternative embodiments, the data set 2 is stored in a database or data storage unit 18 that is separate from the apparatus 12. In this case, the apparatus 12, and specifically the processing unit 14 can access the data set 2 in the data storage unit 18 using interface circuitry 20.

The interface circuitry 20 is for enabling a data connection to and/or data exchange with other devices, including any one or more of sensors, servers, databases (e.g. data storage unit 18), user devices, and the subjects (in embodiments where the subjects are devices or machines). The connection may be direct or indirect (e.g. via the Internet), and thus the interface circuitry 20 can enable a connection between the apparatus 12 and a network, such as the Internet, via any desirable wired or wireless communication protocol. For example, the interface circuitry 20 can operate using WiFi, Bluetooth, Zigbee, or any cellular communication protocol (including but not limited to Global System for Mobile Communications (GSM), Universal Mobile Telecommunications System (UMTS), Long Term Evolution (LTE), LTE-Advanced, etc.). In the case of a wireless connection, the interface circuitry 20 (and thus apparatus 12) may include one or more suitable antennas for transmitting/receiving over a transmission medium (e.g. the air). Alternatively, in the case of a wireless connection, the interface circuitry 20 may include means (e.g. a connector or plug) to enable the interface circuitry 20 to be connected to one or more suitable antennas external to the apparatus 12 for transmitting/receiving over a transmission medium (e.g. the air). The interface circuitry 20 is connected to the processing unit 14 to enable information or data received by the interface circuitry 20 to be provided to the processing unit 14, and/or information or data from the processing unit 14 to be transmitted by the interface circuitry 20 (for example estimated values for the missing parameter values that are to be stored in the data set 2 in the data storage unit 18).

In some embodiments, the apparatus 12 comprises a user interface 22 that includes one or more components that enables a user of apparatus 12 to input information, data and/or commands into the apparatus 12, and/or enables the apparatus 12 to output information or data to the user of the apparatus 12. The user interface 22 can comprise any suitable input component(s), including but not limited to a keyboard, keypad, one or more buttons, switches or dials, a mouse, a track pad, a touchscreen, a stylus, a camera, a microphone, etc., and/or the user interface 22 can comprise any suitable output component(s), including but not limited to a display screen, one or more lights or light elements, one or more loudspeakers, a vibrating element, etc.

The apparatus 12 can be any type of electronic device or computing device. For example the apparatus 12 can be, or be part of, a server, a computer, a laptop, a tablet, a smartphone, a smartwatch, etc. In some implementations, the apparatus 12 is an apparatus that is remote from one or more (or all) of the subjects. Alternatively, for example where the data set 2 relates to the operation of a device or machine, the apparatus 12 may be associated with, or part of the control system of, the device or machine.

It will be appreciated that a practical implementation of an apparatus 12 may include additional components to those shown in FIG. 3. For example the apparatus 12 may also include a power supply, such as a battery, or components for enabling the apparatus 12 to be connected to a mains power supply.

Briefly, the techniques presented herein estimate the value of missing parameter values in a data set 2 by using regression trees. As regression trees are typically constructed using complete data, the proposed techniques dynamically select parameters to use for multiple regression trees from the set of all parameters with respect to the parameter for which a missing value is to be estimated. Particularly, the techniques dynamically determine or select parameters for each missing parameter value imputation based on so-called 'correlation scores' and 'completeness scores'. As described further below, a correlation score indicates a level of correlation between the parameter values in the data set 2 for the parameter of interest (i.e. the parameter with the missing parameter value that is being imputed) and the parameter values in the data set 2 for another one of the parameters, and a completeness score indicates a level of completeness of the data entries 8 in the data subset 4 of interest (i.e. the data subset 4 to which the missing parameter value relates) for the parameter of interest and one of the other parameters. The number of regression trees to use for imputation of the missing parameter value is determined based on the number of selected parameters. The outputs of the multiple regression trees are used for estimating the missing parameter value.

In further embodiments, an average of the values of the parameter of interest over time for all subjects can be determined, which is referred to as a "global average parameter value" or a "feature average", and/or an average of the values of the parameter of interest over time for the subject of interest can be determined (i.e. the subject/data subset 4 with the missing parameter value that is being estimated), which is referred to as a "local average parameter value" or a "time average"), and this average/these averages are combined with the outputs of the regression trees to estimate the missing parameter value. In some embodiments the combination can be a weighted mean, for example determined using a complementary filter.

The estimated missing parameter value can be included in the data set 2, and another missing parameter value estimated using the same techniques (with the data set 2 including any parameter values that have previously been estimated). These techniques can be repeated for each missing parameter value in the data set 2 until all missing parameter values have been estimated.

In further embodiments, after imputing the missing parameter values, the data set 2 is passed through a trained auto encoder to fine tune the imputed/estimated parameter values.

Figure 4:
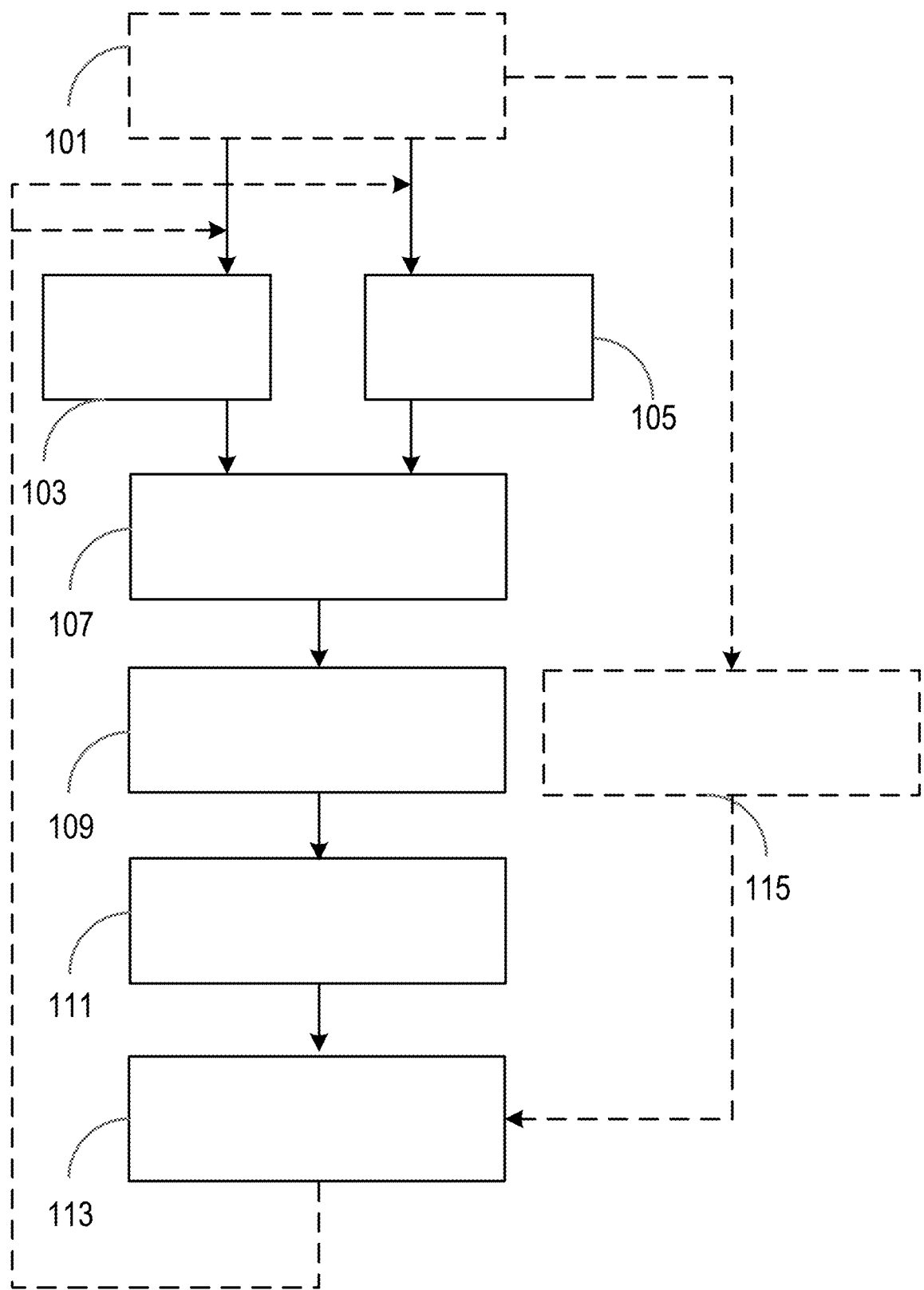
FIG. 4 is a flow chart illustrating a method according to an exemplary embodiment.

The flow chart in FIG. 4 illustrates an exemplary general method according to the techniques described herein for estimating or imputing missing parameter values in a data set 2. One or more of the steps of the method can be performed by the processing unit 14 in the apparatus 12, in conjunction with any of the memory unit 16, interface circuitry 20 and user interface 22 as appropriate. The processing unit 14 may perform the one or more steps in response to executing computer program code, that can be stored on a computer readable medium, such as, for example, the memory unit 16.

In a first step, step 101, the apparatus 12/processing unit 14 receives or obtains a data set 2. The data set 2 has a structure as shown in FIG. 1. The data set 2 relates to a plurality of subjects, and includes a respective data subset 4 for each subject. Each data subset 4 comprises a plurality of data entries corresponding to a respective plurality of time points (sampling points), and each data entry should comprise respective parameter values for each of a plurality of parameters at a respective time point. As noted above, the data set 2 can be a 2DRTS data set 2.

One or more parameter values are missing from the data set 2 obtained or received in step 101. Where a plurality of parameter values are missing from the data set 2, it is possible for a plurality of parameter values to be missing from the same data subset 4, and/or for a plurality of parameter values to be missing for the same parameter. For the purposes of the following discussion, one or more parameter values for at least a first parameter in the plurality of parameters is missing from a first data subset 4 (e.g. a data subset 4 relating to a first subject), and the method in the following steps 103-115 relates to estimating a first missing parameter value in a first data entry in the first data subset 4. It should be noted, however, that the use of 'first' in the following description is merely to clearly identify the parameter value 6, data entry 8 and data subset 4 being considered or discussed, and is not a reference to any order in which the parameter value 6, data entry 8, or data subset 4 exist in the data set 2. Thus, for example, the first missing parameter value can be any missing parameter value in the data set 2, not just a missing parameter value that occurs at the earliest time point.

In some embodiments of step 101, the processing unit 14 can obtain or receive the data set 2 from the memory unit 16 or the separate data storage unit 18. In alternative embodiments, the apparatus 12 may manage and store the data set 2, and thus the apparatus 12/processing unit 14 can obtain or receive parameter values as they are observed or measured and add them to the data set 2. In this case, step 101 can comprise the apparatus 12/processing unit 14 receiving the parameter values over time.

Steps 103-107 of the method determine a number of regression trees and associated parameters to use to estimate the first missing parameter value.

In some embodiments, where multiple parameters in the data set 2 have missing parameter values, the first parameter can be the parameter that has the highest number of missing parameter values, and thus the first missing parameter value can be one of those missing parameter values. Thus, in some embodiments the data set can be analysed to select the first parameter as the parameter having the highest number of missing parameter values.

In step 103, completeness scores are determined for the first parameter. Each completeness score indicates a level of completeness of the data entries 8 in the first data subset 4 for the first parameter and a respective one of the other parameters in the plurality of parameters. For the first parameter, a respective completeness score is determined for each of the other parameters in the plurality. Thus, if there are n parameters in the plurality of parameters, then n–1 completeness scores are determined for the first parameter with each of the other n–1 parameters in the plurality.

In some embodiments, determining a completeness score for two parameters, u (which can be assumed to be the first parameter) and v, can involve determining a number of data entries 8 in the first data subset 4 in which a parameter value for the first parameter and a parameter value for the other parameter are both present. The completeness score for the first parameter may then be determined based on this determined number of data entries 8 relative to a total number of data entries 8 in the first data subset 4. In other words the completeness score for a pair of parameters is a measure of how complete the set of parameter values is for that pair.

Expressed mathematically, a completeness score between the two parameters u and v can be given by:

$$CS(u, v) = \frac{\sum_{i=1}^{m} CB(u_i v_i)}{m} \quad (1)$$

where CB is the binary function defined as:

$$CB(u_i v_i) = \begin{cases} 1 & \text{if } u_i \text{ and } v_i \text{ is not missing} \\ 0 & \text{otherwise} \end{cases} \quad (2)$$

Thus, a completeness score for the two parameters u and v is the average of the value of the binary function CB over the m time samples. The binary function CB has a value 1 if there are parameter values at that time point i for parameters u and v, and 0 otherwise, and the completeness score is the sum of the values of CB for all m time samples, divided by m. Equations (1) and (2) are evaluated for each pair combination of the first parameter and the other parameters in the plurality.

In step 105, which can occur before, after or at generally the same time as step 103, correlation scores are determined for the first parameter. Each correlation score indicates a level of correlation between the parameter values 6 in the data set 2 for the first parameter and the parameter values in the data set 2 for a respective one of the other parameters in the plurality of parameters. For the first parameter, a respective correlation score is determined for each of the other parameters in the plurality. Thus, if there are n parameters in the plurality of parameters, then n–1 correlation scores are determined for the first parameter with each of the other n–1 parameters in the plurality.

In some embodiments, determining a correlation score for the two parameters u and v can involve determining a covariance between the first parameter u and the other parameter v based on the parameter values for the first parameter and the other parameter in the data set 2, determining a standard deviation of the parameter values of the first parameter u in the data set 2, determining a standard deviation of the parameter values of the other parameter v in the data set 2. The correlation score for the first parameter u and the other parameter v is determined from the covariance and standard deviations. In other words the correlation score for a pair of parameters is a measure of how this pair of parameters are mutually related to each other.

Expressed mathematically, a correlation score between the two parameters u and v can be given by:

$$CV(u, v) = \frac{\text{Cov}(u, v)}{\sigma_u \sigma_v} \quad (3)$$

Where Cov(u, v) is the covariance between parameters u and v, and $\sigma_u$ and $\sigma_v$ are the standard deviation of u and v respectively. The covariance Cov(u, v) is given by:

$$\text{Cov}(u,v) = E[(u-\mu_u)(v-\mu_v)] \quad (4)$$

where $\mu_u$ is the mean of u, $\mu_v$ is the mean of v, and E is the expectation or expected value.

Thus, a correlation score for the two parameters u and v is the covariance of the two parameters divided by the product of the standard deviations of the two parameters. Equation (3) is evaluated for each pair combination of the first parameter and the other parameters in the plurality.

It should be noted that the correlation scores are determined using the parameter values across the full data set 2 (which includes multiple data subsets 4), ignoring any missing parameter values, whereas the completeness scores are determined using the parameter values in the data subset 4 (the first data subset 4) that has the missing parameter value of interest, again ignoring any missing parameter values.

Once the completeness scores and the correlation scores have been determined, in step 107 the completeness scores and the correlation scores are used to determine a subset of the plurality of parameters to use to form regression trees. In the next step, step 109, a plurality of regression trees are formed with each regression tree relating to a respective parameter combination of the first parameter and one or more of the other parameters in the subset determined in step 107. Before providing further details of steps 107 and 109, an explanation is provided below that illustrates the motivation for using multiple regression trees rather than a single regression tree to determine the missing parameter value.

Figure 6:
FIG. 6 illustrates exemplary BPSys values associated with the training data.

In particular, a single regression tree cannot be used for imputing missing parameter values in a data set 2 that has a large number of missing parameter values. For example, consider the exemplary data set 10 shown in FIG. 2. This data set 10 is shown as complete, i.e. it does not have any missing parameter values. If a regression tree is formed or constructed to determine, e.g. the systolic blood pressure values, then the training data 30 for the regression tree will have 11 data entries, as shown in FIG. 5, with each data entry 8 having a respective systolic blood pressure 'label' 32 as shown in FIG. 6. A regression tree formed using this training data 30 will work well for estimating systolic blood pressure values if the data set 10 is complete, or if the number of missing systolic blood pressure values is small.

However, consider the exemplary data set 34 shown in FIG. 7, which corresponds to the exemplary data set in FIG. 2, although a significant number of parameter values are missing (as indicated by 'NaN'). In this data set 34, most of the parameters have at least one missing parameter value. If a regression tree is formed or constructed to determine the missing systolic blood pressure values, then, as the training data for the regression tree needs to be complete (i.e. the data entries 8 used in the training data should not include any missing values), the training data 36 for this regression tree can only use the four data entries 8 that are complete, namely data entries 8 corresponding to time points 0, 2, 8 and 9, as shown in FIG. 8. Each of these data entries 8 have a respective systolic blood pressure label 38 as shown in FIG. 9. As the training data 36 includes much less parameter values than the training data 30 for the complete data set 10, a regression tree formed using the training data 38 in FIG. 9 will lead to bias and will not generalise well.

However, it has been recognised that by only using the complete data entries 8 for the training data, some useful information that is present in the data set 2 may not be utilised when training the regression tree. For example, in data set 34 no data entry 8 is missing more than two parameter values, which means that there are at least five parameter values in the remaining seven data entries 8 that might be useful for estimating a missing parameter value.

Steps 107 and 109 operate to form regression trees using the parameter values in incomplete data entries 8 in the data set 2 in order to salvage as much useful data from the data set 2 as possible.

In step 107, as noted above, the completeness scores and the correlation scores are used to determine a subset of the plurality of parameters to use to form regression trees. In some embodiments step 107 comprises, for each of the parameters other than the first parameter (these parameters are referred to herein as 'other parameters'), determining a so-called 'fitness score' for the parameter based on the completeness score for the parameter and the correlation score for the parameter. The fitness score aims to measure the importance of each of the other parameters for filling in a missing value of the first parameter. For a given first parameter, the higher the fitness score of an 'other parameter', the more important the other parameter is to the first parameter. The fitness scores for all of the parameters are used to select the parameters to include in the subset.

In some embodiments, the fitness score for a particular parameter can be determined by multiplying the completeness score for the parameter and the correlation score for the parameter. Alternatively the fitness score for a particular parameter can be determined by summing the completeness score for the parameter and the correlation score for the parameter. Those skilled in the art will be aware of other ways in which a fitness score can be determined from the completeness score and correlation score.

Once the fitness scores have been determined for each of the other parameters, any parameters that have fitness scores above a predetermined threshold are selected for the subset. This results in F parameters being selected for the subset. The predetermined threshold can have any desired value. For example the predetermined threshold can be a percentage of the maximum possible fitness score value, e.g. 60% of the maximum possible fitness score value. In some embodiments the threshold can be set by a user of the method to any desired value. Those skilled in the art will be aware of other ways in which a threshold can be determined.

Next, in step 109, a plurality of regression trees are formed with each regression tree relating to a respective parameter combination of the first parameter and one or more of the other parameters in the subset determined in step 107. Multiple regression trees are used with the aim that at least one of the regression trees is able to provide a useful or reliable output value of the first parameter.

Each regression tree is trained to predict (output) a parameter value for the first parameter based on input parameter values for the one or more other parameters in the parameter combination. The training data that is used to train each regression tree comprises parameter values for the parameters in the respective parameter combination, and in particular the parameter values in any data entry 8 in the first data subset 4 for which a parameter value is present for all of the parameters in the respective parameter combination.

The number of regression trees to form in step 109 can be determined dynamically. In some embodiments the number of regression trees can be determined based on the number F of parameters in the subset. As an example, the number of regression trees can be determined by randomly selecting a number in the range of $(1+F)$ to $P_2^F$. Alternatively the number of regression trees can be determined by non-randomly selecting a number in the above range.

The parameter(s) to be used for a particular regression tree are determined based on the fitness scores for the parameters. The higher the fitness score, the more likely the parameter is to be used for a regression tree, and the more regression trees the parameter will be used with. For example, a first regression tree can be formed to predict a parameter value for the first parameter based on input parameter values for each of the other parameters in the subset. A second regression tree can be formed to predict a parameter value for the first parameter based on input parameter values for the each of other parameters in the parameter combination except the parameter in the subset having the lowest fitness score, and so on.

Figures 10, 11:
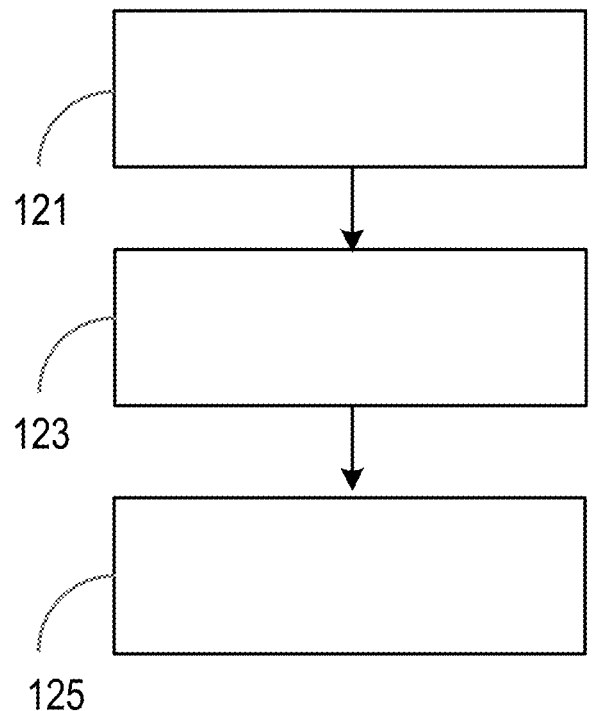
FIG. 10 illustrates an exemplary data entry that has a missing parameter value of interest.
FIG. 11 is a flow chart illustrating a method according to further embodiments.

FIG. 10 shows an exemplary data entry 8 (corresponding to the data entry 8 for time point '6' in FIG. 7). Assuming that the number of regression trees to form is five, if the first parameter is Pulse, then it is not possible to use a regression tree (that is to output a parameter value for Pulse) that has the systolic blood pressure (BPSys) as an input parameter because the value of BPSys is also missing in this data entry 8. However, a regression tree that has the breathing rate (Resp) and temperature (Temp) can be used as the values for these parameters are present in this data entry 8. In this case the training data for this combination (Resp and Temp) comprises all data entries 8 in the first data subset 4 that have parameter values for all of Resp, Temp and Pulse. A regression tree can be used that has diastolic blood pressure (BPDia) and breathing rate (Resp) as input parameters. In this case the training data for this combination (BPDia and Resp) comprises all data entries 8 in the first data subset 4 that have parameter values for all of BPDia, Resp and Pulse.

Once the regression trees have been formed (trained), then in step 111 each regression tree is used to predict a parameter value for the first parameter. In particular, the parameter values in the first data entry (the data entry 8 that includes the missing parameter value that is being determined) are input into the regression trees as appropriate (i.e. based on the input parameters for that regression tree). The output of each regression tree is a value for the missing parameter value in the first data entry. The output of each regression tree is referred to as a 'predicted parameter value'.

In step 113 the predicted parameter values for the missing parameter value are combined to estimate the first missing parameter value.

In some embodiments the predicted parameter values can be combined by determining the average (e.g. mean, median or mode) of the parameter values predicted in the regression tree stage. This combination of the predicted parameter values can be output as the estimate of the first missing parameter value from the regression tree stage. In alternative embodiments, the maximum predicted parameter value or the minimum predicted parameter value can be output as the estimate of the first missing parameter value. The output of the regression tree stage is denoted RT(i,j,k).

In other embodiments of step 113, the predicted parameter values can be combined by determining the average (e.g. mean, median or mode) of the predicted parameter values (or selecting the maximum predicted parameter value or the minimum predicted parameter value output from the regression tree stage), and this combination of the predicted parameter values can be further combined with one or more other estimates of the first missing parameter value. The one or more other estimates can be determined in step 115 as a global average parameter value for the first parameter (which is also referred to as a "feature average" or "feature mean"), and/or a local average parameter value (which is also referred to as a "time average" or "time mean"). The global average parameter value is determined in step 115 from all of the parameter values for the first parameter in the data set 2. Thus, the global average parameter value can be the average (e.g. mean, median or mode) of all of the values of the first parameter in the data set 2. This global average parameter value can also be understood to be a population average, since it is based on the parameter values of the first parameter for all subjects in the data set 2. The local average parameter value is determined in step 115 from all of the parameter values for the first parameter in the first data subset 4, i.e. the data for the subject that has the missing parameter value being estimated. Thus, the local average parameter value can be the average (e.g. mean, median or mode) of all of the values of the first parameter in the first data set 4. This local average parameter value can also be understood to be a subject average, since it is only based on the parameter values of the first parameter for the first subject.

The global average parameter value can be determined from the values of the first parameter in the data set 2 using the following equation:

$$GA(i, j) = \frac{1}{p} \sum_{k=1}^{p} CB(x_{ijk}) \times x_{ijk} \tag{5}$$

The local average parameter value can be determined from the values of the first parameter in the first data subset 4 using the following equation:

$$LA(j, k) = \frac{1}{m} \sum_{i=0}^{m-1} CB(x_{ijk}) \times x_{ijk} \tag{6}$$

In some embodiments, the combined predicted parameter values can be combined with one or both of the global average parameter value and the local average parameter value using a complementary filter to estimate the first missing parameter value.

The complementary filter operates to combine RT(i,j,k) with one or both of GM(i,j,k) and LA(i,j,k), and in particular determines a form of weighted average of the values. In some embodiments the complementary filter can be implemented as follows:

$$CF(i, j, k) = \frac{aRT(i, j, k) + bGA(i, j) + cLA(j, k)}{a + b + c} \tag{7}$$

where a, b and c are constants that determine the weighting provided to each of RT(i,j,k), GM(i,j,k) and LA(i,j,k) in the estimate of the first missing parameter value. Those skilled in the art will appreciate how equation (7) can be modified for embodiments where only one of GM(i,j,k) and LA(i,j,k) is used.

The values of a, b and c can be determined in a number of different ways. In some embodiments the values of a, b and c can be determined based on whether the corresponding parameter has significant observations. In some embodiments, As the values of a, b and c determine the relative contributions of the output of the regression tree stage, the global average parameter value and the local average parameter value to the estimate of the first missing parameter value. These values may be set based on a user preference. For example if the regression trees are considered to provide a better estimate of the first missing parameter value, then the value of weighting a can be set high compared to the value of weighting b and c.

The output of the complementary filter provides the estimated first missing parameter value. This parameter value is then included in the appropriate position in the data set 2 to provide an updated data set.

Regardless of the embodiment of step 113 that is used, the estimated first missing parameter value output by step 113 is referred to as the 'gross estimated first missing parameter value'. The gross estimated first missing parameter value is included in the data set 2 in the appropriate location to provide an updated data set.

If there is another missing parameter value for the first parameter in the first data subset 4 (i.e. in a second data entry 8), then in some embodiments the method in steps 103-115 can then be repeated for this second missing parameter value. It should be noted that the method is repeated with the estimated value of the first missing parameter value included in the data set 2 (i.e. the method is repeated using the updated data set). The method in step 103-115 can be repeated for each missing value of the first parameter in the first data subset 4 until all of the missing values for the first parameter have been estimated and included in the data subset 2.

Once all of the missing values for the first parameter have been estimated, if there is a missing parameter value for another parameter (a 'second parameter') in the first data subset 4, then in some embodiments the method in steps 103-115 can then be repeated to estimate this missing value of the second parameter.

Generally, steps 103-115 are repeated for each missing parameter value in the data set 2 (i.e. across all data subsets 4) until all missing parameter values have been estimated and included in the updated data set.

In some embodiments the updated data set (i.e. including all of the gross estimated missing parameter values) is provided as the final output of the algorithm, and is used for whatever purpose the data set 2 is to be used for (e.g. assessing the health of a patient, assessing the operational or failure status of a device or machine, etc.).

However, in other embodiments, as the estimates determined according to the technique shown in FIG. 4 can accumulate noise and other artefacts as steps 103-115 are repeated for multiple missing parameter values, an auto encoder can be used on the updated data set to refine the gross estimated missing parameter values and provide a refined data set. An auto encoder compresses the input to the auto encoder while aiming to preserve the most essential information in the input, and then decompresses the compressed input to provide an output in which noise and/or artefacts have been reduced, substantially reduced, or eliminated entirely.

The flow chart in FIG. 11 illustrates a method of using an auto encoder according to various embodiments. In step 121, an auto encoder is trained using the non-missing data set to form a trained auto encoder. That is, the auto encoder is trained using all of the complete data entries 8 in the data set 2 (i.e. the data entries 8 that do not have any missing parameter values). So, for example, for the exemplary data set 34 shown in FIG. 7, only the data entries 8 shown in FIG. 8 (plus the corresponding BPSys parameter values from FIG. 7) are used to train the auto encoder. The auto encoder is trained such that the trained auto encoder operates to compress and then decompress input data.

In step 123 the trained auto encoder is used to determine a refined first missing parameter value. In particular, the trained auto encoder receives the updated data set as the input (i.e. the data set 2 including the missing parameter values estimated according to the method in steps 103-115), and outputs a refined data set that has parameter values determined by the auto encoder.

In step 125, a corrected data set is determined from the data set and the refined data set output by the auto encoder. In particular, the corrected data set includes the parameter values that were present in the data set 2 received in step 101, and the parameter value(s) in the refined data set for any missing parameter value in the data set 2 received in step 101. This can be expressed by the following function:

$$X(i, j, k) = \begin{cases} x_{ijk}, & \text{if } CB(x_{ijk}) = 1 \\ (x')_{ijk}, & \text{if } CB(x_{ijk}) = 0 \end{cases} \quad (8)$$

where $X(i,j,k)$ is the corrected data set, and $x'_{ijk}$ is the parameter value for i,j,k in the refined data set output by the auto encoder. Thus, equation (8) has the effect that the parameter values corresponding to the missing parameter values in the data set 2 that are estimated by the auto encoder are used in place of the missing parameter values estimated in steps 103-113 above.

The corrected data set $X(i,j,k)$ is the final output of the algorithm in FIGS. 4 and 11, and is used for whatever purpose the data set 2 is to be used for (e.g. assessing the health of a patient, assessing the operational or failure status of a device or machine, etc.).

Figure 12:
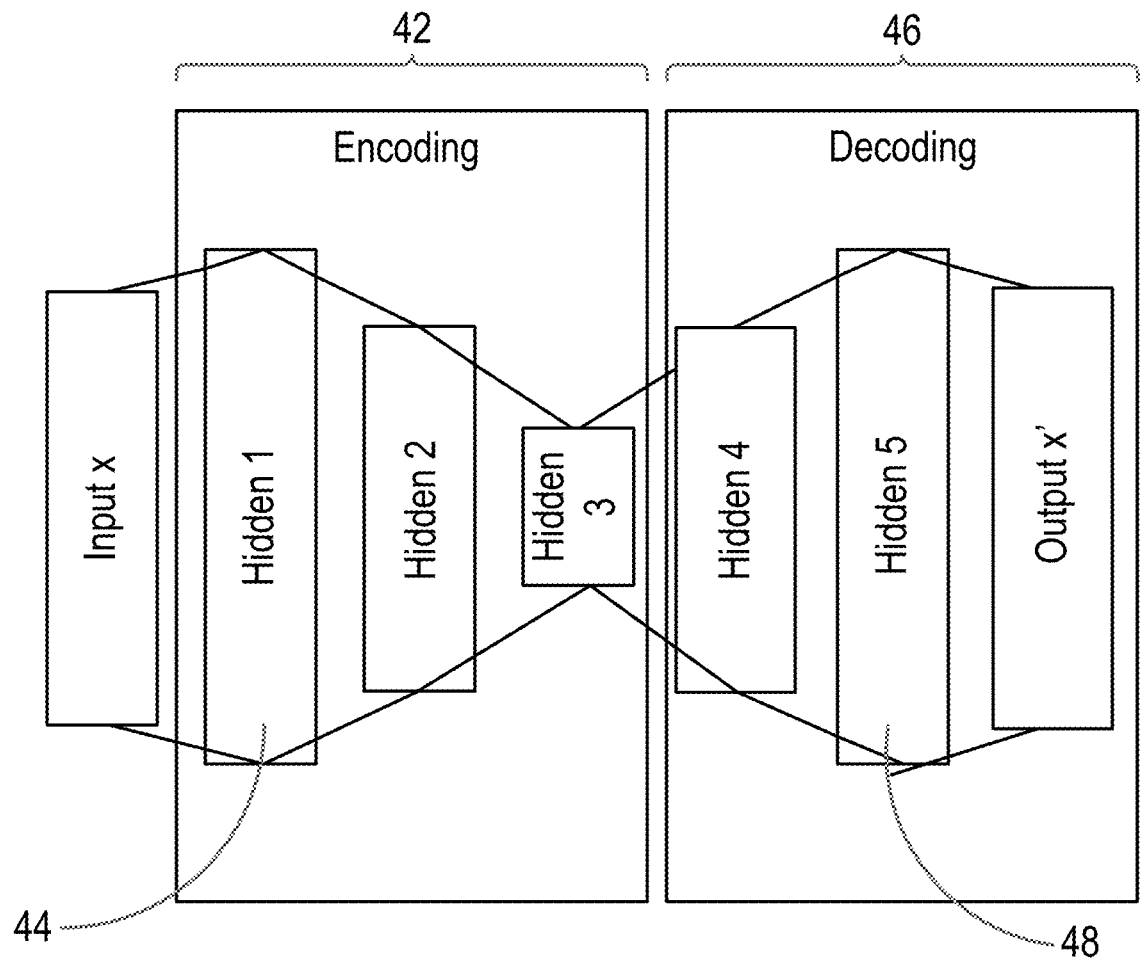
FIG. 12 illustrates a stacked auto encoder according to various embodiments.

FIG. 12 is an illustration of an auto encoder 40 that can be used in the above embodiments. The auto encoder 40 may be a stacked auto encoder 40. The auto encoder 40 includes an encoding stage 42 that operates to compress the input to the auto encoder 40 while preserving the most essential information in the input. The encoding stage 42 includes at least one hidden layer 44 (and preferably a plurality of hidden layers 44), and in the illustrated embodiment the encoding stage 42 includes three hidden layers 44. The number of neurons in the first hidden layer 44 (Hidden layer 1) should be greater than number of parameter values in the updated data set that is to be input to the auto encoder 40, as this has been found to be better in removing noise in the estimated missing parameter values in the updated data set. In this illustrated embodiment, the encoding stage 42 includes three hidden layers 44, with each hidden layer 44 further compressing the output of the previous hidden layer 44.

The auto encoder 40 also includes a decoding stage 46 that decompresses the compressed input to reconstruct the input, thereby reducing, substantially reducing or eliminating noise and/or other artefacts in the input. The decoding stage 46 includes at least one hidden layer 48 (and preferably a plurality of hidden layers 48), and in the illustrated embodiment the decoding stage 46 includes two hidden layers 48.

A trained auto encoder 40 will have weights at each connection that joins each pair of adjacent layers 44, 48.

In some embodiments, in addition to estimating missing parameter values as described above, the methods presented above can also be used to correct parameter values in the data set 2 that are corrupt. For these purposes, a corrupt parameter value is a parameter value that is out of range for the particular parameter. For example a negative heart rate value is corrupt, and a diastolic blood pressure value of 400 mmHg is corrupt. Corrupt parameter values can occur during transmission of the parameter value over a network, due to faulty sensors, due to incorrect data entry for a user (e.g. healthcare provider). Thus, to correct corrupt parameter values, after the data set is received or obtained in step 101 the processing unit 14 evaluates each of the parameter values in the data set 2 against a criteria for the respective parameter. The criteria can be an upper bound for the values of the parameter, a lower bound for the values of the parameter, or a predetermined range for the values of the parameter. Any parameter value that does not meet the criteria (e.g. the parameter value exceeds the upper bound, the parameter value is below the lower bound or the parameter value is outside the predetermined range) is deemed 'corrupt' and is discarded from the data set 2 and treated as a missing parameter value. The corrupt parameter value is therefore not used in any of steps 103-115 of FIG. 4 and steps 121-125 of FIG. 11. Instead, the corrupt parameter value is estimated using the method in FIG. 4, and optionally in FIG. 11. In some embodiments, the data set 2 received or obtained in step 101 may not include any missing parameter values, but one or more of the parameter values may be determined to be corrupt and discarded from the data set 2. In that case the method of FIG. 4 (and optionally FIG. 11) operates to estimate the parameter value for the corrupt parameter value(s).

Therefore the techniques described above provide improvements in the estimation of missing values in a data set. In particular the techniques make use of correlation information across dependent parameters (i.e. parameters whose values have some dependency on the values of other parameters) and builds a plurality of regression trees to provide respective estimates of the missing parameter value. In this way, the amount of information in the data set that is used to estimate the missing parameter value is improved relative to conventional approaches that uses a single regression tree formed only from complete data entries in the data set.

A worked example of the techniques presented above is now described with reference to FIGS. 7 and 13-15. This worked example is based on the first data subset 4 shown in FIG. 7. The data set 2 comprises seven parameters, and the first data subset 4 has 11 data entries 8. The parameters BPSys, Pulse and Weight are all missing three parameter values in the first data subset 4. In this example, a missing value for Pulse is to be determined, and in particular the value for Pulse in the final data entry 8 (time sample 10).

According to step 103 of the method in FIG. 4, a completeness score for the Pulse with each of the other parameters is determined according to equations (1) and (2). The completeness scores are as follows: BPDia=0.64, BPSys=0.55, Height=0.64, Resp=0.64, Temp=0.73 and Weight=0.45. For example, for the completeness score with BPDia, there are 7 data entries that have both a Pulse value and a BPDia value, which gives a completeness score of 7/11. As noted above, each completeness score indicates a level of completeness of the data entries 8 in the first data subset 4 for the Pulse and the respective one of the other parameters.

According to step 105 of the method in FIG. 4, a correlation score for the Pulse with each of the other parameters is determined according to equation (3). The correlation score are as follows: BPDia=0.7, BPSys=0.8, Height=0.1, Resp=0.6, Temp=0.2 and Weight=0.05. As noted above, each correlation score indicates a level of correlation between the parameter values 6 in the full data set 2 (so not just the first data subset 4) for the Pulse and the parameter values in the data set 2 for the respective one of the other parameters.

According to step 107, the completeness scores and the correlation scores are used to determine a subset of the parameters to use to form regression trees. Therefore a fitness score can be determined for each of the other parameters by multiplying the respective completeness score and respective correlation score. This results in fitness scores of: BPDia=0.44, BPSys=0.43, Height=0.06, Resp=0.38, Temp=0.14 and Weight=0.02.

With a predetermined threshold of 0.3, it can be seen that the fitness scores of three of the parameters exceed the predetermined threshold, namely BPDia, BPSys and Resp, and these three parameters therefore form the subset.

In step 109, the number of regression trees to be formed is determined to be F+1, so four in this example. However it will be appreciated that more regression trees can be formed if desired. Each regression tree relates to the Pulse and one or more of the parameters in the subset, and the training data for each regression tree comprises the parameter values for the relevant parameters in any data entry 8 in the first data subset 4 for which a parameter value is present for all of the relevant parameters.

FIG. 13 illustrates the four regression trees in terms of the parameters and the training data from the first data subset 4 that is used to train each regression tree. Thus, the first regression tree in FIG. 13(a) has BPSys, BPDia and Resp as input parameters, and there are five data entries 8 in the first data subset 4 where parameter values are present for each of these three parameters and Pulse. The second regression tree in FIG. 13(b) has BPSys and BPDia as input parameters, and there are six data entries 8 in the first data subset 4 where parameter values are present for each of these two parameters and Pulse. The third regression tree in FIG. 13(c) just has BPSys as the input parameter, and there are six data entries 8 in the first data subset 4 where parameter values are present for BPSys and Pulse. The fourth regression tree in FIG. 13(d) just has BPDia as the input parameter, and there are seven data entries 8 in the first data subset 4 where parameter values are present for BPDia and Pulse.

Next, according to step 111, each regression tree is used to predict a value of the pulse at time sample 10. Thus, parameter values in the data entry 8 corresponding to time sample 10 are input into the regression trees as appropriate. It can be seen in FIG. 7 that for time sample 10, Resp is also missing, so the first regression tree in FIG. 13(a) is not able to provide a value for the pulse. However, the other three regression trees in FIGS. 13(b)-(d) each provide a predicted pulse value for time sample 10. Regression tree 2 provides a pulse value of 74, regression tree 3 provides a pulse value of 76 and regression tree 4 provides a pulse value of 75. These predicted pulse values are averaged to give an estimated pulse of 75.

According to embodiments of steps 113 and 115, this averaged predicted value is combined with a global average pulse value (75 in this example) and a local average pulse value (also 75 in this example) using a complementary filter which gives a pulse value of 75.

This pulse value is added to the data set 2, and the method is repeated for all of the other missing pulse values, and then all of the missing values for the other parameters. FIG. 14 shows the updated data set 50 that includes all of the estimated missing parameter values.

According to step 121, an auto encoder 40 is trained using all of the complete data entries 8 in the data set 2. Thus, the auto encoder 40 is trained based on data entries 8 corresponding to time samples 0, 2, 8 and 9 in the first data subset 4 shown in FIG. 7, and any complete data entries 8 in other data subsets 4 of the data set 2.

Then, according to step 123 the updated data set 50 in FIG. 14 is input to the trained auto encoder 40, and a refined data set is output.

Using equation (8), the corrected data set is formed from the original data set 2 and the parameter values corresponding to the missing parameter values in the refined data set output by the auto encoder 40. FIG. 15 shows the corrected data set 52 that is produced using equation (8) and the output of the auto encoder 40.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method for processing a data set, the data set comprising respective data subsets for a plurality of subjects, each data subset comprising a plurality of data entries corresponding to a respective plurality of time points, each data entry comprising respective parameter values for a plurality of parameters at the corresponding respective time point, wherein for a first data subset relating to a first subject in the plurality of subjects, one or more parameter values for at least a first parameter in the plurality of parameters is missing from the first data subset, the method comprising, for a first missing parameter value in a first data entry in the first data subset:

(a) determining completeness scores for the first parameter, wherein each completeness score indicates a level of completeness of the data entries in the first data subset for the first parameter and respective ones of other parameters in the plurality of parameters;

(b) determining correlation scores for the first parameter, wherein each correlation score indicates a level of correlation between the parameter values in the data set for the first parameter and the parameter values in the data set for respective ones of the other parameters in the plurality of parameters;

(c) determining a subset of the plurality of parameters to use to form regression trees based on the determined completeness scores and the determined correlation scores;

(d) forming a plurality of regression trees, wherein each regression tree relates to a respective parameter combination of the first parameter and one or more other parameters in the determined subset, and each regression tree is trained to predict a parameter value for the first parameter based on input parameter values for the one or more other parameters in the respective parameter combination, wherein each regression tree is trained using training data comprising parameter values for the parameters in the respective parameter combination, wherein the training data includes the parameter values in any data entry in the first data subset for which a parameter value is present for all of the parameters in the respective parameter combination;

(e) using each regression tree to predict a parameter value for the first parameter based on parameter values in the first data entry for the one or more other parameters in the respective parameter combination; and (f) combining the predicted parameter values to estimate the first missing parameter value.

2. The method as claimed in claim 1, further comprising: determining at least one of:
a global average parameter value for the first parameter from all of the parameter values for the first parameter in the data set; or
a local average parameter value for the first parameter from all of the parameter values for the first parameter in the first data subset; and
wherein combining the predicted parameter values comprises:
combining the predicted parameter values and the determined at least one of the global average parameter value or the local average parameter value to estimate the first missing parameter value.

3. The method as claimed in claim 1, wherein determining the completeness scores for the first parameter comprises, for each of the other parameters:

determining a number of data entries in the first data subset in which a parameter value for the first parameter and a parameter value for the other parameter are both present.

4. The method as claimed in claim 1, wherein determining the correlation scores for the first parameter comprises, for each of the other parameters:
determining a covariance between the first parameter and the other parameter based on the parameter values for the first parameter and the other parameter in the data set;
determining a standard deviation of the parameter values of the first parameter in the data set and a standard deviation of the parameter values of the other parameter in the data set; and
determining the correlation score for the first parameter and the other parameter from the determined covariance and determined standard deviations.

5. The method as claimed in claim 1, wherein determining the subset of the plurality of parameters to use to form regression trees comprises:
determining a fitness score for each of the other parameters based on the completeness score for the other parameter and the correlation score for the other parameter; and
selecting other parameters for the subset based on determined fitness score for the other parameters.

6. The method as claimed in claim 1, further comprising:
updating the data set to include the estimated first missing parameter value.

7. The method as claimed in claim 6, further comprising:
repeating steps (a)-(f) for at least a second missing parameter value in a second data entry in the first data subset, wherein the second missing parameter value is a parameter value of the first parameter, and wherein steps (a)-(f) are repeated using the data set updated with the estimated first missing parameter value; and
updating the data set to include the estimated second missing parameter value.

8. The method as claimed in claim 6, further comprising:
repeating steps (a)-(f) for at least a third missing parameter value in a third data entry in the first data subset, wherein the third missing parameter value is a parameter value for another one of the plurality of parameters the first data subset for which a parameter value is missing, and wherein steps (a)-(f) are repeated using the data set with previously estimated missing parameter values; and
updating the data set to include the estimated third missing parameter value.

9. The method as claimed in claim 6, further comprising:
repeating steps (a)-(f) for each missing parameter value in the data set, wherein steps (a)-(f) are repeated using the data set updated with previously estimated missing parameter values; and
updating the data set to include each estimated missing parameter value.

10. The method as claimed in claim 9, further comprising:
using a trained auto encoder to determine a refined first missing parameter value, wherein the auto encoder receives as input the data set updated with each of the estimated missing parameter values.

11. The method as claimed in claim 10, further comprising:
training an auto encoder using an auto encoder training data set to form the trained auto encoder, wherein the auto encoder is trained such that the trained auto encoder operates to compress and then decompress the data set updated with each of the estimated missing parameter values; wherein the auto encoder training data set comprises data entries in the data set for which parameter values are present for all of the parameters.

12. The method as claimed in claim 11, wherein using the auto encoder comprises the auto encoder compressing and decompressing the data set updated with each of the estimated missing parameter values to determine a refined data set;

wherein the method further comprises:
determining a corrected data set from the data set and the determined refined data set, wherein the corrected data set comprises the parameter values in the data set and the parameter values in the refined data set for the missing parameter values in the data set.

13. The method as claimed claim 1, wherein prior to step (a), the method further comprises:
evaluating each of the parameter values in the data set against a criteria for the respective parameter that determines whether the parameter value is corrupt; and
discarding any parameter value from the data set that is determined to be corrupt, and treating the discarded parameter value as a missing parameter value.

14. A non-transitory computer readable medium storing computer readable instructions for processing a data set, the data set comprising respective data subsets for a plurality of subjects, each data subset comprising a plurality of data entries corresponding to a respective plurality of time points, each data entry comprising respective parameter values for a plurality of parameters at the corresponding respective time point, wherein for a first data subset relating to a first subject in the plurality of subjects, one or more parameter values for at least a first parameter in the plurality of parameters is missing from the first data subset, wherein on execution by a suitable computer or processor, the computer readable instructions cause the suitable computer or processor to, for a first missing parameter value in a first data entry in the first data subset:
(a) determine completeness scores for the first parameter, wherein each completeness score indicates a level of completeness of the data entries in the first data subset for the first parameter and respective ones of other parameters in the plurality of parameters;
(b) determine correlation scores for the first parameter, wherein each correlation score indicates a level of correlation between the parameter values in the data set for the first parameter and the parameter values in the data set for respective ones of other parameters in the plurality of parameters;
(c) determine a subset of the plurality of parameters to use to form regression trees based on the determined completeness scores and the determined correlation scores;
(d) form a plurality of regression trees, wherein each regression tree relates to a respective parameter combination of the first parameter and one or more other parameters in, the determined subset, and each regression tree is trained to predict a parameter value for the first parameter based on input parameter values for the one or more other parameters in the respective parameter combination, wherein each regression tree is trained using training data comprising parameter values for the parameters in the respective parameter combination, wherein the training data includes the parameter values in any data entry in the first data subset for which a parameter value is present for all of the parameters in the respective parameter combination;

(e) use each regression tree to predict a parameter value for the first parameter based on parameter values in the first data entry for the one or more other parameters in the respective parameter combination; and
(f) combine the predicted parameter values to estimate the first missing parameter value.

15. An apparatus for processing a data set, the data set comprising respective data subsets for a plurality of subjects, each data subset comprising a plurality of data entries corresponding to a respective plurality of time points, each data entry comprising respective parameter values for a plurality of parameters at the corresponding respective time point, wherein for a first data subset relating to a first subject in the plurality of subjects, one or more parameter values for at least a first parameter in the plurality of parameters is missing from the first data subset, the apparatus comprising a processing unit configured to, for a first missing parameter value in a first data entry in the first data subset:
(a) determine completeness scores for the first parameter, wherein each completeness score indicates a level of completeness of the data entries in the first data subset for the first parameter and respective ones of other parameters in the plurality of parameters;
(b) determine correlation scores for the first parameter, wherein each correlation score indicates a level of correlation between the parameter values in the data set for the first parameter and the parameter values in the data set for respective ones of other parameters in the plurality of parameters;
(c) determine a subset of the plurality of parameters to use to form regression trees based on the determined completeness scores and the determined correlation scores;
(d) form a plurality of regression trees, wherein each regression tree relates to a respective parameter combination of the first parameter and one or more other parameters in the determined subset, and each regression tree is trained to predict a parameter value for the first parameter based on input parameter values for the one or more other parameters in the respective parameter combination, wherein each regression tree is trained using training data comprising parameter values for the parameters in the respective parameter combination, wherein the training data includes the parameter values in any data entry in the first data subset for which a parameter value is present for all of the parameters in the respective parameter combination;
(e) use each regression tree to predict a parameter value for the first parameter based on parameter values in the first data entry for the one or more other parameters in the respective parameter combination; and
(f) combine the predicted parameter values to estimate the first missing parameter value.

16. The apparatus as claimed in claim 15, wherein the processing unit is further configured to:
determine at least one of:
a global average parameter value for the first parameter from all of the parameter values for the first parameter in the data set; or
a local average parameter value for the first parameter from all of the parameter values for the first parameter in the first data subset; and
combine the predicted parameter values by combining the predicted parameter values and the determined at least one of the global average parameter value or the local average parameter value to estimate the first missing parameter value.

17. The apparatus as claimed in claim 15, wherein the processing unit is configured to determine the completeness scores for the first parameter comprises, for each of the other parameters by determining a number of data entries in the first data subset in which a parameter value for the first parameter and a parameter value for the other parameter are both present.

18. The apparatus as claimed in claim 15, wherein the processing unit is configured to determine the correlation scores for the first parameter comprises, for each of the other parameters by:
 determining a covariance between the first parameter and the other parameter based on the parameter values for the first parameter and the other parameter in the data set;
 determining a standard deviation of the parameter values of the first parameter in the data set and a standard deviation of the parameter values of the other parameter in the data set; and
 determining the correlation score for the first parameter and the other parameter from the determined covariance and determined standard deviations.

19. The apparatus as claimed in claim 15, wherein the processing unit is configured to determine the subset of the plurality of parameters to use to form regression trees by:
 determining a fitness score for each of the other parameters based on the completeness score for the other parameter and the correlation score for the other parameter; and
 selecting other parameters for the subset based on determined fitness score for the other parameters.

20. The apparatus as claimed in claim 15, wherein the processing unit is further configured to:
 update the data set to include the estimated first missing parameter value.

\* \* \* \* \*